(12) United States Patent
Frey

(10) Patent No.: US 6,673,552 B2
(45) Date of Patent: Jan. 6, 2004

(54) METHODS FOR PURIFYING ANNEALED DOUBLE-STRANDED OLIGONUCLEOTIDES LACKING BASE PAIR MISMATCHES OR NUCLEOTIDE GAPS

(75) Inventor: Gerhard Frey, San Diego, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 10/077,474

(22) Filed: Feb. 14, 2002

(65) Prior Publication Data

US 2003/0134289 A1 Jul. 17, 2003

Related U.S. Application Data

(60) Provisional application No. 60/348,609, filed on Jan. 14, 2002.

(51) Int. Cl.[7] .......................... C12Q 1/68; C07H 21/04; C07K 17/00; C12P 21/04
(52) U.S. Cl. .......................... 435/6; 536/23.1; 530/350; 435/69.7
(58) Field of Search .......................... 435/6, 69.7, 91.2; 530/350; 536/23.1, 25.32

(56) References Cited

U.S. PATENT DOCUMENTS

| | | | |
|---|---|---|---|
| 5,556,750 A | | 9/1996 | Modrich et al. .............. 435/6 |
| 5,750,335 A | * | 5/1998 | Gifford .......................... 435/6 |
| 6,046,036 A | * | 4/2000 | Kelley et al. ............... 435/69.7 |
| 6,114,115 A | * | 9/2000 | Wagner, Jr. ..................... 435/6 |
| 6,294,325 B1 | * | 9/2001 | Wetmur ......................... 435/6 |
| 6,297,010 B1 | * | 10/2001 | Stefano ........................ 435/6 |
| 6,333,153 B1 | | 12/2001 | Fishel et al. ................... 435/6 |
| 6,365,355 B1 | * | 4/2002 | McCutchen-Maloney ...... 435/6 |

FOREIGN PATENT DOCUMENTS

WO    WO 96/41192    12/1996

OTHER PUBLICATIONS

Myers, et al., "Detection of Single Base Substitutions by Ribonuclease Cleavage at Mismatches in RNA:DNA Duplexes", Science 230:1242–1246; 1985.

Su & Modrich, "*Escherichia coli* mutS–encoded Protein Binds to Mismatched DNA Base Pairs", Proc. Natl. Acad. Sci 83:5057–5061; Jul. 1986.

Lu, et al.; "Detection of Single DNA Based Mutations with Mismatch Repair Enzymes", Genomics 14:249–255; 1992.

Biswas, et al., "Interaction of MutS Protein with the Major and Minor Grooves of a Heteroduplex DNA", J. Biol. Chem, 272:13355–13364; 1997.

* cited by examiner

*Primary Examiner*—Gary Benzion
*Assistant Examiner*—Cynthia Wilder
(74) *Attorney, Agent, or Firm*—James E. Butler; Diversa Patent Dept.

(57) ABSTRACT

The invention provides methods for identifying and purifying double-stranded polynucleotides lacking base pair mismatches, insertion/deletion loops and/or nucleotide gaps.

34 Claims, No Drawings

METHODS FOR PURIFYING ANNEALED DOUBLE-STRANDED OLIGONUCLEOTIDES LACKING BASE PAIR MISMATCHES OR NUCLEOTIDE GAPS

RELATED APPLICATIONS

This application claims the benefit of priority under 35 U.S.C. §119(e) of U.S. Provisional Application No. 60/348,609, filed Jan. 14, 2002. The aforementioned application is explicitly incorporated herein by reference in its entirety and for all purposes.

TECHNICAL FIELD

The present invention is generally directed to the fields of genetic and protein engineering and molecular biology. In particular, the invention provides methods for identifying and purifying double-stranded polynucleotides lacking base pair mismatches, insertion/deletion loops and nucleotide gaps.

BACKGROUND

Synthetic oligonucleotides are commonly used to construct nucleic acids, including polypeptide coding sequences and gene constructs. However, even the best oligonucleotide synthesizer has a 1% to 5% error rate. These errors can result in improper base pair sequences, which can lead to generation of an erroneous protein sequences. These errors can also result in sequences that cannot be properly transcribed or untranslated, including, e.g., premature stop codons. To detect these errors, the oligonucleotides or the sequences generated using the oligonucleotides are sequenced. However, sequencing to detect errors in nucleic acid synthetic techniques is time consuming and expensive.

SUMMARY

The invention provides a method for purifying double-stranded polynucleotides lacking base pair mismatches, insertion/deletion loops and/or nucleotide gaps comprising the following steps: (a) providing a plurality of polypeptides that specifically bind to a base pair mismatch, an insertion/deletion loop and/or a nucleotide gap or gaps within a double stranded polynucleotide; (b) providing a sample comprising a plurality of double-stranded polynucleotides; (c) contacting the double-stranded polynucleotides of step (b) with the polypeptides of step (a) under conditions wherein a polypeptide of step (a) can specifically bind to a base pair mismatch, an insertion/deletion loop and/or a nucleotide gap or gaps in a double stranded polynucleotide of step (b); and (d) separating the double-stranded polynucleotides lacking a specifically bound polypeptide of step (a) from the double-stranded polynucleotides to which a polypeptide of step (a) has specifically bound, thereby purifying double-stranded polynucleotides lacking base pair mismatches, insertion/deletion loops and/or nucleotide gaps. In one aspect, the double-stranded polynucleotide comprises a double-stranded oligonucleotide.

In alternative aspects, the double-stranded polynucleotide is between about 3 and about 300 base pairs in length; between 10 and about 200 base pairs in length; and, between 50 and about 150 base pairs in length. In alternative aspects, the gaps in the double-stranded polynucleotide are between about 1 and 30, about 2 and 20, about 3 and 15, about 4 and 12 and about 5 and 10 nucleotides in length.

In alternative aspects, thee the base pair mismatch comprises a C:T mismatch, a G:A mismatch, a C:A mismatch or a G:U/T mismatch.

In one aspect, the polypeptide that specifically binds to a base pair mismatch, an insertion/deletion loop and/or a nucleotide gap or gaps in a double stranded polynucleotide comprises a DNA repair enzyme. In alternative aspects, the DNA repair enzyme is a bacterial DNA repair enzyme, a MutS DNA repair enzyme, a Taq MutS DNA repair enzyme, an Fpg DNA repair enzyme, a MutY DNA repair enzyme, a hexA DNA mismatch repair enzyme, a Vsr mismatch repair enzyme, a mammalian DNA repair enzyme and natural or synthetic variations and isozymes thereof. In one aspect, the DNA repair enzyme is a DNA glycosylase that initiates base-excision repair of G:U/T mismatches. The DNA glycosylase can comprise a bacterial mismatch-specific uracil-DNA glycosylase (MUG) DNA repair enzyme or a eukaryotic thymine-DNA glycosylase (TDG) enzyme.

In one aspect, the separating of the double-stranded polynucleotides lacking a specifically bound polypeptide of step (a) from the double-stranded polynucleotides to which a polypeptide of step (a) has specifically bound of step (d) comprises use of an immunoaffinity column, wherein the column comprises immobilized antibodies capable of specifically binding to the specifically bound polypeptide or an epitope bound to the specifically bound polypeptide, and the sample is passed through the immunoaffinity column under conditions wherein the immobilized antibodies are capable of specifically binding to the specifically bound polypeptide or the epitope bound to the specifically bound polypeptide.

In one aspect, the separating of the double-stranded polynucleotides lacking a specifically bound polypeptide of step (a) from the double-stranded polynucleotides to which a polypeptide of step (a) has specifically bound of step (d) comprises use of an antibody, wherein the antibody is capable of specifically binding to the specifically bound polypeptide or an epitope bound to the specifically bound polypeptide and the antibody is contacted with the specifically bound polypeptide under conditions wherein the antibodies are capable of specifically binding to the specifically bound polypeptide or an epitope bound to the specifically bound polypeptide. The antibody can be an immobilized antibody. The antibody can be immobilized onto a bead or a magnetized particle or a magnetized bead.

In one aspect, the separating of the double-stranded polynucleotides lacking a specifically bound polypeptide of step (a) from the double-stranded polynucleotides to which a polypeptide of step (a) has specifically bound of step (d) comprises use of an affinity column, wherein the column comprises immobilized binding molecules capable of specifically binding to a tag linked to the specifically bound polypeptide and the sample is passed through the affinity column under conditions wherein the immobilized antibodies are capable of specifically binding to the tag linked to the specifically bound polypeptide. The immobilized binding molecules can comprise an avidin or a natural or synthetic variation or homologue thereof and the tag linked to the specifically bound polypeptide can comprise a biotin or a natural or synthetic variation or homologue thereof.

In one aspect, the separating of the double-stranded polynucleotides lacking a specifically bound polypeptide of step (a) from the double-stranded polynucleotides to which a polypeptide of step (a) has specifically bound of step (d) comprises use of a size exclusion column, such as a spin column. Alternatively, the separating can comprise use of a size exclusion gel, such as an agarose gel.

In one aspect, the double-stranded polynucleotide comprises a polypeptide coding sequence. The polypeptide coding sequence can comprise a fusion protein coding sequence. The fusion protein can comprise a polypeptide of interest upstream of an intein, wherein the intein comprises a polypeptide. The intein polypeptide can comprise an enzyme, such as one used to identify vector or insert positive clones, such as Lac Z. The intein polypeptide can comprise an antibody or a ligand. In one aspect, the intein polypeptide comprises a polypeptide selectable marker, such as an antibiotic. The antibiotic can comprise a kanamycin, a penicillin or a hygromycin.

The invention provides a method for assembling double-stranded oligonucleotides to generate a polynucleotide lacking base pair mismatches, insertion/deletion loops and/or nucleotide gaps comprising the following steps: (a) providing a plurality of polypeptides that specifically bind to a base pair mismatch, an insertion/deletion loop and/or a nucleotide gap or gaps in a double stranded polynucleotide; (b) providing a sample comprising a plurality of double-stranded oligonucleotides; (c) contacting the double-stranded oligonucleotides of step (b) with the polypeptides of step (a) under conditions wherein a polypeptide of step (a) can specifically bind to a base pair mismatch, an insertion/ deletion loop and/or a nucleotide gap or gaps in a double stranded oligonucleotide of step (b); (d) separating the double-stranded oligonucleotides lacking a specifically bound polypeptide of step (a) from the double-stranded oligonucleotides to which a polypeptide of step (a) has specifically bound, thereby purifying double-stranded oligonucleotides lacking base pair mismatches, insertion/ deletion loops and/or a nucleotide gap or gaps; and (e) joining together the purified double-stranded oligonucleotides lacking base pair mismatches and insertion/deletion loops, thereby generating a polynucleotide lacking base pair mismatches, insertion/deletion loops and/or nucleotide gaps.

The invention provides a method for generating a polynucleotide lacking base pair mismatches, insertion/deletion loops and/or nucleotide gaps comprising the following steps: (a) providing a plurality of polypeptides that specifically bind to a base pair mismatch, an insertion/deletion loop and/or a nucleotide gap or gaps in a double stranded polynucleotide; (b) providing a sample comprising a plurality of double-stranded oligonucleotides; (c) joining together the double-stranded oligonucleotides of step (b) to generate a double-stranded polynucleotide; (d) contacting the double-stranded polynucleotide of step (c) with the polypeptides of step (a) under conditions wherein a polypeptide of step (a) can specifically bind to a base pair mismatch, an insertion/ deletion loop and/or a nucleotide gap or gaps in a double stranded polynucleotide of step (c); and (e) separating the double-stranded polynucleotides lacking a specifically bound polypeptide of step (a) from the double-stranded polynucleotides to which a polypeptide of step (a) has specifically bound, thereby purifying double-stranded polynucleotides lacking base pair mismatches, insertion/deletion loops and/or nucleotide gaps.

The invention provides a method for generating a base pair mismatch-free, insertion/deletion loop-free and/or gap-free double-stranded polypeptide coding sequence comprising the following steps: (a) providing a plurality of polypeptides that specifically bind to a base pair mismatch, an insertion/deletion loop and/or a nucleotide gap or gaps within a double stranded polynucleotide; (b) providing a sample comprising a plurality of double-stranded polynucleotides encoding a fusion protein, wherein the fusion protein coding sequence comprises a coding sequence for a polypeptide of interest upstream of and in frame with a coding sequence for a marker or a selection polypeptide; (c) contacting the double-stranded polynucleotides of step (b) with the polypeptides of step (a) under conditions wherein a polypeptide of step (a) can specifically bind to a base pair mismatch, an insertion/deletion loop and/or a nucleotide gap or gaps in a double stranded polynucleotide of step (b); (d) separating the double-stranded polynucleotides lacking a specifically bound polypeptide of step (a) from the double-stranded polynucleotides to which a polypeptide of step (a) has specifically bound, thereby purifying double-stranded polynucleotides lacking base pair mismatches, insertion/ deletion loops and/or a nucleotide gap or gaps; (e) expressing the purified double-stranded polynucleotides and selecting the polynucleotides expressing the selection marker polypeptide, thereby generating a base pair mismatch-free, insertion/deletion loop-free and/or gap-free double-stranded polypeptide coding sequence.

In one aspect, the marker or selection polypeptide comprises a self-splicing intein, and the method further comprises the self-splicing out of the intein marker or selection polypeptide from the upstream polypeptide of interest. The marker or selection polypeptide can comprise an enzyme, such as a enzyme used to identity insert or vector-positive clones, such as a LacZ enzyme. The marker or selection polypeptide can also comprise an antibiotic, such as a kanamycin, a penicillin or a hygromycin.

In alternative aspects of the invention, the methods generate a sample or "batch" of purified oligonucleotides and/or polynucleotides that are 90%, 95%, 96%, 97%, 98%, 99%, 99.5% and 100% or completely free of base pair mismatches, insertion/deletion loops and/or a nucleotide gap or gaps.

The details of one or more embodiments of the invention are set forth in the accompanying drawings and the description below. Other features, objects, and advantages of the invention will be apparent from the description and drawings, and from the claims.

DETAILED DESCRIPTION

The invention provides methods for identifying and purifying double-stranded polynucleotides lacking nucleotide gaps, base pair mismatches and insertion/deletion loops.

Definitions

Unless defined otherwise, all technical and scientific terms used herein have the meaning commonly understood by a person skilled in the art to which this invention belongs. As used herein, the following terms have the meanings ascribed to them unless specified otherwise.

The phrase "polypeptides that specifically bind to a nucleotide gap or gaps, a base pair mismatch and/or an insertion/deletion loop in a double stranded polynucleotide" include all polypeptides, natural or synthetic, that can specifically bind to a nucleoside base pair mismatch, an insertion/ deletion loop and/or a nucleotide gap or gaps in a double stranded polynucleotide (e.g., oligonucleotide). These polypeptides include, e.g., DNA repair enzymes, antibodies, transcriptional regulatory polypeptides and the like, as described in further detail, below. These polypeptides can be isolated, recombinant or synthetically derived. They can be modeled from polypeptides found in nature or they can artificially designed, e.g., in silico. These polypeptides include peptidomimetics, polypeptide analogs and the like. Specifically binds or specific binding means any level of affinity of binding that is not non-specific.

The phrase "lacking base pair mismatches, insertion/ deletion loops and/or a nucleotide gap or gaps" means substantially lacking or completely lacking base pair mismatches, insertion/deletion loops and/or a nucleotide gap or gaps. For example, the methods of the invention can generate a sample or "batch" of purified oligonucleotides and/or polynucleotides that are about 90%, about 95%, about 96%, about 97%, about 98%, about 99%, about 99.5%, about 99.9% and 100% or completely free of base pair mismatches, insertion/deletion loops and/or nucleotide gaps.

The phrase "DNA repair enzymes" includes all DNA repair enzymes and natural or synthetic (e.g., genetically reengineered) variations thereof that can specifically bind to a base pair mismatch, an insertion/deletion loop and/or a nucleotide gap or gaps in a double stranded polynucleotide (e.g., oligonucleotide), including, e.g., DNA mismatch repair (MMR) enzymes, Taq MutS enzymes, Fpg enzymes, MutY DNA repair enzymes, hexA DNA mismatch repair enzymes, Vsr mismatch repair enzymes and the like, as described in further detail, below.

The term "MutS DNA repair enzyme" includes all MutS DNA repair enzymes, including synthetic (e.g., genetically reengineered) variations, and eukaryotic (e.g., mammalian) homologues of bacterial enzymes, that can bind a nucleoside base pair mismatch or an insertion/deletion loop, including, e.g., the *Thermus aquaticus* (Taq) and *Pseudomonas aeruginosa* MutS DNA repair enzymes, as described in further detail, below.

The term "Fpg DNA repair enzyme" includes all Fpg DNA repair enzymes, including synthetic (e.g., genetically reengineered) variations, and eukaryotic (e.g., mammalian) homologues of bacterial enzymes, that can bind a nucleoside base pair mismatch or an insertion/deletion loop, as described in further detail, below.

The term "MutY" includes all MutY DNA repair enzymes, including synthetic (e.g., genetically reengineered) variations, and eukaryotic (e.g., mammalian) homologues of bacterial enzymes, that can bind a nucleoside base pair mismatch or an insertion/deletion loop, as described in further detail, below The term "DNA glycosylase" includes all natural or synthetic DNA glycosylase enzymes that initiate base-excision repair of G:U/T mismatches. The natural DNA glycosylase enzymes include, e.g., bacterial mismatch-specific uracil-DNA glycosylase (MUG) DNA repair enzymes and eukaryotic thymine-DNA glycosylase (TDG) enzymes, as described in further detail, below.

The term "intein" includes all polypeptide sequences that are self-splicing. Inteins are intron-like elements that are removed post-translationally by self-splicing, as described in further detail, below.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

The terms "nucleic acid" and "polynucleotide" as used herein refer to a deoxyribonucleotide or ribonucleotide in either single- or double-stranded form. The terms encompass all nucleic acids, e.g., oligonucleotides, and modifications analogues of natural nucleotides, e.g., nucleic acids with modified internucleoside linkages. The terms also encompass nucleic-acid-like structures with synthetic backbones. Synthetic backbone analogues include, e.g., phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units, and can be used as probes (see, e.g., U.S. Pat. No. 5,871,902). Phosphorothioate linkages are described, e.g., in WO 97/03211; WO 96/39154; Mata (1997) Toxicol. Appl. Pharmacol. 144:189–197. Other synthetic backbones include methyl-phosphonate linkages or alternating methylphosphonate and phosphodiester linkages (Strauss-Soukup (1997) Biochemistry 36:8692–8698), and benzylphosphonate linkages (Samstag (1996) Antisense Nucleic Acid Drug Dev 6:153–156). Modified internucleoside linkages that are resistant to nucleases are described, e.g., in U.S. Pat. No. 5,817,781. The term nucleic acid can be used interchangeably with the terms gene, cDNA, mRNA, probe and amplification product.

The invention provides a method for purifying double-stranded polynucleotides lacking base pair mismatches, insertion/deletion loops and/or nucleotide gaps comprising providing a plurality of polypeptides that specifically bind to a base pair mismatch, an insertion/deletion loop and/or nucleotide gaps within a double stranded polynucleotide. The methods of the invention can use any polypeptide, natural or synthetic, that specifically binds to a base pair mismatch, an insertion/deletion loop and/or a nucleotide gap or gaps in a double stranded polynucleotide. This includes all polypeptides, natural or synthetic, that can specifically bind to a nucleoside base pair mismatch, an insertion/deletion loop and/or a nucleotide gap or gaps in a double stranded polynucleotide, such as a double stranded oligonucleotide. The polypeptide can be, e.g., an enzyme, a structural protein, an antibody, variations thereof, or a protein of entirely synthetic, e.g., in silico, design. These polypeptides include, e.g., DNA repair enzymes and transcriptional regulatory polypeptides and the like. In one aspect, the mismatch or insertion/deletion loop is not within the extreme 5' or 3' end of the double stranded nucleic acid.

DNA repair enzymes can include all DNA repair enzymes and natural or synthetic (e.g., genetically reengineered) variations thereof that can specifically bind to a base pair mismatch, an insertion/deletion loop and/or a nucleotide gap or gaps in a double stranded polynucleotide. Examples include, e.g., DNA mismatch repair (MMR) enzymes (see, e.g., Hsich (2001) Mutat. Res. 486(2):71–87), Taq MutS enzymes, Fpg enzymes, MutY DNA repair enzymes, hexA DNA mismatch repair enzymes (see, e.g., Ren (2001) Curr. Microbiol. 43:232–237), Vsr mismatch repair enzymes (see, e.g., Mansour (2001) Mutat. Res. 485(4):331–338) and the like. See, e.g., Mol (1999) Annu. Rev. Biophys. Biomol. Struct. 28:101–128; Obmolova (2000) Nature 407(6805): 703–710.

MutS DNA repair enzymes include all MutS DNA repair enzymes, including synthetic (e.g., genetically reengineered) variations, and eukaryotic (e.g., mammalian)

homologues of bacterial enzymes, that can bind a nucleoside base pair mismatch or an insertion/deletion loop, including, e.g., the *Thermus aquaticus* (Taq) and *Pseudomonas aeruginosa* MutS DNA repair enzymes. The MutS DNA repair enzyme can be used in the form of a dimer. For example, it can be a homodimer of a MutS homolog, e.g., a human MutS homolog, a murine MutS homolog, a rat MutS homolog, a Drosophila MutS homolog, a yeast MutS homolog, such as a *Saccharomyces cerevisiae* MutS homolog. See, e.g., U.S. Pat. No. 6,333,153; Pezza (2002) Biochem J. 361(Pt 1):87–95; Biswas (2001) J. Mol. Biol. 305:805–816; Biswas (2000) Biochem J. 347 Pt 3:881–886; Biswas (1999) J. Biol. Chem. 274:23673–23678. MutS has been shown to preferentially bind a nucleic acid heteroduplex containing a deletion of a single base, see, e.g., Biwas (1997) J. Biol. Chem. 272:13355–13364; see also, Su (1986) Proc. Natl. Acad. Sci. 83:5057–5061; Malkov (1997) J. Biol. Chem. 272:23811–23817.

Fpg DNA repair enzymes includes all Fpg DNA repair enzymes, including synthetic (e.g., genetically reengineered) variations, and eukaryotic (e.g., mammalian) homologues of bacterial enzymes, that can bind a nucleoside base pair mismatch or an insertion/deletion loop, including, e.g., the Fgp enzyme from *Escherichia coli*. See, e.g., Leipold (2000) Biochemistry 39:14984–14992.

MutY DNA repair enzymes include all MutY DNA repair enzymes, including synthetic (e.g., genetically reengineered) variations, and eukaryotic (e.g., mammalian) homologues of bacterial enzymes, that can bind a nucleoside base pair mismatch or an insertion/deletion loop (see, e.g., Porello (1998) Biochemistry 37:14756–14764; Williams (1999) Biochemistry 38:15417–15424).

DNA glycosylase includes all natural or synthetic DNA glycosylase enzymes that initiate base-excision repair of G:U/T mismatches. The natural DNA glycosylase enzymes form a homologous family of DNA glycosylase enzymes that initiate base-excision repair of G:U/T mismatches, including, e.g., bacterial mismatch-specific uracil-DNA glycosylase (MUG) DNA repair enzymes (see, e.g., Barrett (1999) EMBO J. 18:6599–6609) and eukaryotic thymine-DNA glycosylase (TDG) enzymes (see, e.g., Barrett (1999) ibid; Barrett (1998) Cell 92:117–129). See also Pearl (2000) Mutat. Res. 460:165–181; Niederreither (1998) Oncogene 17:1577–15785.

Additional nucleotide gap binding polypeptides include, e.g., DNA polymerase deltas, such as the DNA polymerase delta isolated in the teleost fish *Misgurnus fossilis* (see, e.g., Sharova (2001) Biochemistry (Mosc) 66:402–409); DNA polymerase betas, see, e.g., Bhattacharyya (2001) Biochemistry 40:9005–9013; DNA topoisomerases, such as type IB DNA topoisomerase V, as in the hyperthermophile *Methanopyrus kandleri* described by Belova (2001) Proc. Natl. Acad. Sci. USA 98:6015–6020; ribosomal proteins, e.g., S3 ribosomal proteins such as the Drosophila S3 ribosomal protein described by Hegde (2001) J. Biol. Chem. 276:27591–2756.

The methods of the invention comprise contacting the double-stranded polynucleotides with the polypeptides to be purified of base pair mismatches, insertion/deletion loops and/or a nucleotide gap or gaps under conditions wherein a mismatch-, an insertion/deletion loop- and/or a gap-binding polypeptide can specifically bind to a base pair mismatch or an insertion/deletion loop or a nucleotide gap or gaps. These conditions are well known in the art, as described, e.g., in the references cited herein, or, can be determined or optimized by one skilled in the art without undue experimentation. For example, U.S. Pat. No. 6,333,153, describes a method comprising contacting a MutS dimer and the mismatched duplex DNA in the presence of a binding solution comprising ADP and optionally ATP. The concentration of ATP, if present, in the binding solution is less than about 3 micromolar. The MutS dimer binds ADP, and the MutS ADP-bound dimer associates with a mismatched region of the duplex DNA.

In mammalian cells most altered bases in DNA are repaired through a single-nucleotide patch base excision repair mechanism. Base excision repair is initiated by a DNA glycosylase that removes a damaged base and generates an a basic site (AP site). This AP site is further processed by an AP endonuclease activity that incises the phosphodiester bond adjacent to the AP site and generates a strand break containing 3'-OH and 5'-sugar phosphate ends. In mammalian cells, the 5'-sugar phosphate is removed by the AP lyase activity of DNA polymerase beta. The same enzyme also fills the gap, and the DNA ends are finally rejoined by DNA ligase. Thus, in addition to DNA polymerases such as DNA polymerase beta, the methods of the invention also can use DNA glycosylases as oligonucleotide or polynucleotide binding polypeptides alone or in conjunction with other base pair mismatch-, insertion/deletion loop- or nucleotide gap-binding polypeptides. See, e.g., Podlutsky (2001) Biochemistry 40:809–813.

Marker and Selection Polypeptides

The invention provides a methods comprising purifying a double-stranded polynucleotide lacking base pair mismatches, insertion/deletion loops and/or a nucleotide gap or gaps, wherein the polynucleotide encodes a fusion protein coding sequence that comprises a coding sequence for a polypeptide of interest upstream of and in frame with a coding sequence for a marker or a selection polypeptide. The use of a marker or a selection polypeptide coding sequence downstream of and in frame with a polypeptide of interest acts to confirm that the polypeptide of interest coding sequence lacks defects that would prevent transcription or translation of the fusion protein sequence. Because the marker or a selection polypeptide coding sequence is downstream and in frame with the polypeptide of interest coding sequence, any such defects would prevent transcription and/or translation of the marker or selection polypeptide. For example, this scheme can be used to segregate or purify out polypeptide of interest coding sequences lacking base pair mismatches, insertion/deletion loops and/or a nucleotide gap or gaps from those with a defect that would prevent transcription or translation of the sequence, the defect including, e.g., base pair mismatches, insertion/deletion loops and/or gap(s).

Selection markers can be incorporated to confer a phenotype to facilitate selection of cells transformed with the sequences purified by the methods of the invention. For example, a marker selection polypeptide can comprise an enzyme, e.g., LacZ encoding a polypeptide with beta-galactosidase activity which, when expressed in a transformed cell and exposed to the appropriate substrate will produce a detectable marker, e.g., a color. See, e.g., Jain (1993) Gene 133:99–102; St Pierre (1996) Gene 169:65–68; Pessi (2001) Microbiology 147(Pt 8):1993–1995. See also U.S. Pat. Nos. 5,444,161; 4,861,718; 4,708,929; 4,668,622. Selection markers can code for episomal maintenance and replication such that integration into the host genome is not required. Selection markers can code for chloramphenicol acetyl transferase (CAT); an enzyme-substrate reaction is monitored by addition of an exogenous electron carrier and a tetrazolium salt. See, e.g., U.S. Pat. No. 6,225,074.

The marker can also encode antibiotic, herbicide or drug resistance to permit selection of those cells transformed with the desired DNA sequences. For example, antibiotic resistance can be conferred by herpes simplex thymidine kinase (conferring resistance to ganciclovir), chloramphenicol resistance enzymes (see, e.g., Harrod (1997) Nucleic Acids Res. 25:1720–1726), kanamycin resistance enzymes, aminoglycoside phosphotransferase (conferring resistance to G418), bleomycin resistance enzymes, hygromycin resistance enzymes, and the like. The marker can also encode a herbicide resistance, e.g., chlorosulfuron or Basta. Because selectable marker genes conferring resistance to substrates like neomycin or hygromycin can only be utilized in tissue culture, chemoresistance genes are also used as selectable markers in vitro and in vivo. The marker can also encode enzymes conferring resistance to a drug, e.g., an oubain-resistant (Na, K)-ATPase; a MDR1 multidrug transporter (confers resistance to certain cytotoxic drugs), and the like. Various target cells are rendered resistant to anticancer drugs by transfer of chemoresistance genes encoding P-glycoprotein, the multidrug resistance-associated protein-transporter, dihydrofolate reductase, glutathione-S-transferase, O6-alkylguanine DNA alkyltransferase, or aldehyde reductase. See, e.g., Licht (1995) Cytokines Mol. Ther. 1:11–20; Blondelet-Rouault (1997) Gene 190:315–317; Aubrecht (1997) J. Pharmacol. Exp. Ther. 281:992–997; Licht (1997) Stem Cells 15:104–111; Yang (1998) Clin. Cancer Res. 4:731–741. See also U.S. Pat. No. 5,851,804, describing chimeric kanamycin resistance genes; U.S. Pat. No. 4,784,949.

The marker or selection polypeptide can also comprise a sequence coding for a polypeptide with affinity to a known antibody to facilitate affinity purification, detection, or the like. Such detection- and purification-facilitating domains include, but are not limited to, metal chelating peptides such as polyhistidine tracts and histidine-tryptophan modules that allow purification on immobilized metals, protein A or biotin domains that allow purification, e.g., on immobilized immunoglobulin or streptavidin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the protein of interest and the second domain can also be used, e.g., to facilitate purification and for ease of handling and using the protein of interest. For example, a fusion protein can comprise six histidine residues followed by thioredoxin and an enterokinase cleavage site (for example, see Williams (1995) Biochemistry 34:1787–1797). The histidine residues facilitate detection and purification while the enterokinase cleavage site provides a means for purifying the desired protein of interest from the remainder of the fusion protein. Technology pertaining to vectors encoding fusion proteins and application of fusion proteins are well described in the patent and scientific literature, see e.g., Kroll (1993) DNA Cell. Biol., 12:441–53.

Inteins

In one aspect, the marker or selection polypeptide coding sequence can be a self-splicing intein. Inteins are intron-like elements that are removed post-translationally by self-splicing. Thus, the methods of the invention can further comprise the self-splicing out of the marker or selection polypeptide intein coding sequence from the polypeptide of interest. Intein sequences are well known in the art. See, e.g., Colston (1994) Mol. Microbiol. 12:359–363; Perler (1994) Nucleic Acids Res. 22:1125–1127; Perler (1997) Curr. Opin. Chem. Biol. 1:292–299; Giriat (2001) Genet. Eng. (NY) 23:171–199. See also, U.S. Pat. Nos. 5,795,731; 5,496,714. For example, because inteins are protein splicing elements that occur naturally as in-frame protein fusions, intein sequences can be designed or based on naturally occurring intein sequences. Inteins are phylogenetically widespread, having been found in all three biological kingdoms, eubacteria, archaea and eukaryotes. Alternatively, they entirely synthetic splicing sequences. Intein nomenclature parallels that for RNA splicing, whereby the coding sequences of a gene (exteins) are interrupted by sequences that specify the protein splicing element (intein).

Purifying Error Free Polynucleotides

In one aspect, the methods of the invention comprise purifying double-stranded polynucleotides lacking a base pair mismatch-, an insertion/deletion loop and/or a nucleotide gap or gaps. Any purification methodology can be used, including use of antibodies, binding molecules, size exclusion and the like.

Antibodies and Immunoaffinity Columns

In one aspect, antibodies are used to purify a double-stranded polynucleotide lacking a base pair mismatch-, an insertion/deletion loop or a nucleotide gap or gaps. For example, antibodies can be designed to specifically bind directly to a base pair mismatch-, insertion/deletion loop- or nucleotide gap-binding polypeptide, or, antibodies can bind to an epitope bound to the base pair mismatch-, insertion/deletion loop- or nucleotide gap-binding polypeptide. The antibody can be bound to a bead, such as a magnetized bead. See, e.g., U.S. Pat. Nos. 5,981,297; 5,508,164; 5,445,971; 5,445,970. See also, U.S. Pat. Nos. 5,858,223; 5,746,321, and, 6,312,910, describing a multistage electromagnetic separator to separate magnetically susceptible materials suspended in fluids.

The separating can comprise use of an immunoaffinity column, wherein the column comprises immobilized antibodies capable of specifically binding to the specifically bound base pair mismatch-, insertion/deletion loop- or nucleotide gap-binding polypeptide or an epitope bound to the base pair mismatch-, insertion/deletion loop- or nucleotide gap-binding polypeptide. The sample is passed through an immunoaffinity column under conditions wherein the immobilized antibodies are capable of specifically binding to the specifically bound polypeptide or the epitope, or "tag," bound to the specifically bound polypeptide.

Monoclonal or polyclonal antibodies to base pair mismatch-, insertion/deletion loop-binding and/or a nucleotide gap-binding polypeptides can be used. Methods of producing polyclonal and monoclonal antibodies are known to those of skill in the art and described in the scientific and patent literature, see, e.g., Coligan, Current Protocols in Immunology, Wiley/Greene, N.Y. (1991); Stites (eds.) Basic and Clinical Immunology (7th ed.) Lange Medical Publications, Los Altos, Calif. ("Stites"); Goding, Monoclonal Antibodies: Principles and Practice (2d ed.) Academic Press, New York, N.Y. (1986); Kohler (1975) Nature 256:495; Harlow (1988) Antibodies, a Laboratory Manual, Cold Spring Harbor Publications, New York. Antibodies also can be generated in vitro, e.g., using recombinant antibody binding site expressing phage display libraries, in addition to the traditional in vivo methods using animals. See, e.g., Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267–273; Yarmush (1992) J. Biochem. Biophys. Methods 25:85–97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Single chain antibodies are also included by reference in the term "antibody."

Biotin/Avidin Separation Systems

Any ligand/receptor model can be used to purify a double-stranded polynucleotide lacking a base pair mismatch-, an insertion/deletion loop and/or a nucleotide gap or gaps. For example, a biotin can be attached to a base pair mismatch-, an insertion/deletion loop- and/or a nucleotide gap binding polypeptide, or, it can be part of a fusion protein comprising a base pair mismatch-, an insertion/deletion loop- and/or a nucleotide gap-binding polypeptide. The biotin-binding avidin is typically immobilized, e.g., onto a bead, a magnetic material, a column, a gel and the like. The bead can be magnetized. See, e.g., the U.S. Patents noted above for making and using magnetic particles in purification techniques, and, describing various biotin-avidin binding systems and methods for making and using them, U.S. Pat. Nos. 6,287,792; 6,277,609; 6,214,974; 6,022,688; 5,484,701; 5,432,067; 5,374,516.

Generating and Manipulating Nucleic Acids

The invention provides methods for purifying double-stranded polynucleotides lacking base pair mismatches, insertion/deletion loops and/or a nucleotide gap or gaps. Nucleic acids purified by the methods of the invention can be amplified, cloned, sequence or further manipulated, e.g., their sequences can be further changed by SLR, GSSM and the like. The polypeptides used in the methods of the invention can be expressed recombinantly, synthesized or isolated from natural sources. These and other nucleic acids needed to make and use the invention can be isolated from a cell, recombinantly generated or made synthetically. The sequences can be isolated by, e.g., cloning and expression of cDNA libraries, amplification of message or genomic DNA by PCR, and the like. In practicing the methods of the invention, genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Left. 22:1859; U.S. Pat. No. 4,458,066.

Techniques for the manipulation of nucleic acids, such as, e.g., subcloning, ligations, labeling probes (e.g., random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1–3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Amplification of Nucleic Acids

In practicing the methods of the invention, nucleic acids can be generated and reproduced by, e.g., amplification reactions. Amplification reactions can also be used to join together nucleic acids to generate fusion protein coding sequences. Amplification reactions can also be used to clone sequences into vectors. Amplification reactions can also be used to quantify the amount of nucleic acid in a sample, label the nucleic acid (e.g., to apply it to an array or a blot), detect the nucleic acid, or quantify the amount of a specific nucleic acid in a sample. Message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

A number of embodiments of the invention have been described. Nevertheless, it will be understood that various modifications may be made without departing from the spirit and scope of the invention. Accordingly, other embodiments are within the scope of the following claims.

What is claimed is:

1. A method for purifying double-stranded polynucleotides lacking base pair mismatches, insertion/deletion loops and/or a nucleotide gap or gaps comprising the following steps:
   (a) providing a plurality of polypeptides that specifically bind to a base pair mismatch, an insertion/deletion loop and/or a nucleotide gap or gaps within a double stranded polynucleotide comprising a Vsr (very short patch repair) bacterial DNA mismatch repair enzyme;
   (b) providing a sample comprising a plurality of double-stranded polynucleotides;
   (c) contacting the double-stranded polynucleotides of step (b) with the polypeptides of step (a) under conditions wherein a polypeptide of step (a) can specifically bind to a base pair mismatch, an insertion/deletion loop and/or a nucleotide gap or gaps in a double-stranded polynucleotide of step (b); and
   (d) separating the double-stranded polynucleotides lacking a specifically bound polypeptide of step (a) from the double-stranded polynucleotides to which a polypeptide of step (a) has specifically bound, thereby purifying double-stranded polynucleotides lacking base pair mismatches, insertion/deletion loops and/or a nucleotide gap or gaps.

2. The method of claim 1, wherein a polypeptide that specifically binds to a base pair mismatch, an insertion/deletion loop or a nucleotide gap further comprises a biotin molecule.

3. The method of claim 1, wherein a polypeptide that specifically binds to a base pair mismatch, an insertion/deletion loop or a nucleotide gap further comprises a molecule comprising an epitope binds specifically to an antibody.

4. The method of claim 1, wherein the insertion/deletion loop comprises a stem-loop structure.

5. The method of claim 1, wherein the insertion/deletion loop comprises a single base pair mismatch.

6. The method of claim 5, wherein the insertion/deletion loop comprises two consecutive base pair mismatches.

7. The method of claim 6, wherein the insertion/deletion loop comprises three consecutive base pair mismatches.

8. The method of claim 1, wherein the separating of the double-stranded polynucleotides lacking a specifically bound polypeptide of step (a) from the double-stranded polynucleotides to which a polypeptide of step (a) has specifically bound of step (d) comprises use of an antibody, wherein the antibody binds specifically to the specifically bound polypeptide or an epitope bound to the specifically bound polypeptide and the antibody is contacted with the specifically bound polypeptide under conditions wherein the antibodies can specifically bind to the specifically bound polypeptide or an epitope bound to the specifically bound polypeptide.

9. The method of claim 8, wherein the antibody is an immobilized antibody.

10. The method of claim 9, wherein the antibody is immobilized onto a bead or a magnetized particle.

11. The method of claim 10, wherein the antibody is immobilized onto a magnetized bead.

12. The method of claim 9, wherein the antibody is an immobilized in an immunoaffinity column and the sample is passed through the immunoaffinity column under conditions wherein the immobilized antibodies are capable of specifically binding to the specifically bound polypeptide or the epitope bound to the specifically bound polypeptide.

13. The method of claim 1, wherein the separating of the double-stranded polynucleotides lacking a specifically bound polypeptide of step (a) from the double-stranded polynucleotides to which a polypeptide of step (a) has specifically bound of step (d) comprises use of an affinity column, wherein the column comprises immobilized binding molecules that specifically bind to a tag linked to the specifically bound polypeptide and the sample is passed through the affinity column under conditions wherein the immobilized antibodies can specifically bind to the tag linked to the specifically bound polypeptide.

14. The method of claim 13, wherein the immobilized binding molecules comprise an avidin and the tag linked to the specifically bound polypeptide comprises a biotin.

15. The method of claim 1, wherein the separating of the double-stranded polynucleotides lacking a specifically bound polypeptide of step (a) from the double-stranded polynucleotides to which a polypeptide of step (a) has specifically bound of step (d) comprises use of a size exclusion column.

16. The method of claim 15, wherein the size exclusion column comprises a spin column.

17. The method of claim 1, wherein the separating of the double-stranded polynucleotides lacking a specifically bound polypeptide of step (a) from the double-stranded polynucleotides to which a polypeptide of step (a) has specifically bound of step (d) comprises use of a size exclusion gel.

18. The method of claim 17, wherein the size exclusion gel comprises an agarose gel.

19. The method of claim 1, wherein the double-stranded polynucleotide comprises a polypeptide coding sequence.

20. The method of claim 19, wherein the polypeptide coding sequence comprises a fusion protein coding sequence.

21. A method for purifying double-stranded polynucleotides lacking base pair mismatches, insertion/deletion loops and/or a nucleotide gap or gaps comprising the following steps:
   (a) providing a plurality of polypeptides that specifically bind to a base pair mismatch, an insertion/deletion loop and/or a nucleotide gap or gaps within a double-stranded polynucleotide;
   (b) providing a sample comprising a plurality of double-stranded polynucleotides encoding a fusion protein comprising a polypeptide of interest upstream of an intein, wherein the intein encodes a polypeptide;
   (c) contacting the double-stranded polynucleotides of step (b) with the polypeptides of step (a) under conditions wherein a polypeptide of step (a) can specifically bind to a base pair mismatch, an insertion/deletion loop and/or a nucleotide gap or gaps in a double-stranded polynucleotide of step (b); and
   (d) separating the double-stranded polynucleotides lacking a specifically bound polypeptide of step (a) from the double-stranded polynucleotides to which a polypeptide of step (a) has specifically bound, thereby purifying double-stranded polynucleotides lacking base pair mismatches, insertion/deletion loops and/or a nucleotide gap or gaps.

22. The method of claim 21, wherein the intein polypeptide comprises an antibody or a ligand.

23. The method of claim 21, wherein the intein polypeptide comprises an enzyme.

24. The method of claim 23, wherein the enzyme comprises Lac Z.

25. The method of claim 21, wherein the intein polypeptide comprises a polypeptide selectable marker.

26. The method of claim 25, wherein the polypeptide selectable marker comprises an antibiotic.

27. The method of claim 26, wherein the antibiotic comprises a kanamycin, a penicillin or a hygromycin.

28. A method for purifying double-stranded polynucleotides lacking base pair mismatches, insertion/deletion loops and/or a nucleotide gap or gaps comprising:
  (a) providing a plurality of polypeptides that specifically bind to a base pair mismatch, an insertion/deletion loop and/or a nucleotide gap or gaps within a double stranded polynucleotide;
  (b) providing a sample comprising a plurality of double-stranded polynucleotides encoding a fusion protein comprising a polypeptide of interest and an intein, wherein the intein encodes a polypeptide;
  (c) contacting the double-stranded polynucleotides of (b) with the polypeptides of (a) under conditions wherein a polypeptide of (a) can specifically bind to a base pair mismatch, an insertion/deletion loop and/or a nucleotide gap or gaps in a double stranded polynucleotide of (b); and
  (d) separating the double-stranded polynucleotides lacking a specifically bound polypeptide of (a) from the double-stranded polynucleotides to which a polypeptide of (a) has specifically bound, thereby purifying double-stranded polynucleotides lacking base pair mismatches, insertion/deletion loops and/or a nucleotide gap or gaps.

29. The method of claim 28, wherein the intein polypeptide comprises an antibody or a ligand.

30. The method of claim 28, wherein the intein polypeptide comprises an enzyme.

31. The method of claim 30, wherein the enzyme comprises Lac Z.

32. The method of claim 28, wherein the intein polypeptide comprises a polypeptide selectable marker.

33. The method of claim 32, wherein the polypeptide selectable marker comprises an antibiotic.

34. The method of claim 33, wherein the antibiotic comprises a kanamycin, a penicillin or a hygromycin.

* * * * *

UNITED STATES PATENT AND TRADEMARK OFFICE
Certificate

Patent No. 6,673,552 B2                            Patented: January 6, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gerhard Frey, San Diego, CA (US); Lilian Parra-Gessert, San Diego, CA (US); and Angela Kennedy, Ontario, Canada.

Signed and Sealed this Thirty-first Day of July 2007.

WILLIAM R. DIXON, JR.
*Special Program Examiner*
Technology Center 1600